United States Patent [19]

Bock

[11] 4,389,525

[45] Jun. 21, 1983

[54] PROCESS FOR THE RESOLUTION OF SOME INTERPHENYLENE 9-THIA-11-OXO-12-AZAPROSTANOIC ACIDS

[75] Inventor: Mark G. Bock, Hatfield, Robert M. Di Pardo, Lansdale, both of Pa.

[73] Assignee: Merck & Co., Inc., Rahway, N.J.

[21] Appl. No.: 276,116

[22] Filed: Jun. 22, 1981

[51] Int. Cl.³ ............................................. C07D 277/04
[52] U.S. Cl. ..................................... 548/187; 548/186
[58] Field of Search .......................................... 548/187

[56] References Cited

U.S. PATENT DOCUMENTS 4,225,609 9/1980 Cragoe et al. ...................... 424/270

OTHER PUBLICATIONS

B. Halpern et al., Chem. Abstracts 65: 19996e (1966).
Gerlach, Helv., Chem. Acta 51, 1587–1593 (1968).

Primary Examiner—Nicholas S. Rizzo
Assistant Examiner—M. C. Easkin
Attorney, Agent, or Firm—Alice O. Robertson; Ernest V. Linek; Daniel I. Szura

[57] ABSTRACT

A process for resolving certain interphenylene-9-thia-11-oxo-12-azaprostanoic acids using camphanic or a camphor carboxylic acid, certain intermediates and optically pure azaprostanoic acids are disclosed.

3 Claims, No Drawings

PROCESS FOR THE RESOLUTION OF SOME INTERPHENYLENE 9-THIA-11-OXO-12-AZAPROSTANOIC ACIDS

BACKGROUND OF THE INVENTION

Resolution is the process whereby a racemic modification, be it racemic mixture, racemic compound or racemic solution, is separated into its enantiomers. The most popular method consists in converting the enantiomers of a racemic modification into diastereoisomers.

The racemic modification is reacted with an optically active substance which in turn is separated by fractional crystallization or chromatography. Thus, e.g. racemic acids may be separated by optically active bases, and racemic alcohols resolved by optically active acids or derivatives thereof.

Interphenylene-9-thia-11-oxo-12-azaprostanoic acids having pharmaceutical activity are described in U.S. Pat. No. 4,225,609. It has now been discovered that racemic mixtures of these acids can be resolved to provide individual enantiomers of the acids using camphanic acid or a camphor carboxylic acid as the resolving agent. The resolution proceeds through formation of ester diastereomers, separation of the diastereomers and subsequent hydrolysis to obtain the enantiomer acid.

SUMMARY OF THE INVENTION

A process for resolving compounds illustrated by the formula:

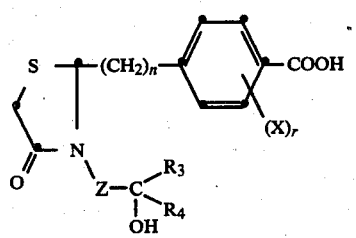

I using camphanic acid or a camphor carboxylic acid as the resolving agent, diastereomer esters of I and enantiomers of I.

DETAILED DESCRIPTION OF THE INVENTION

The present invention is embodied in a process for resolving certain azaprostanoic acids of the formula:

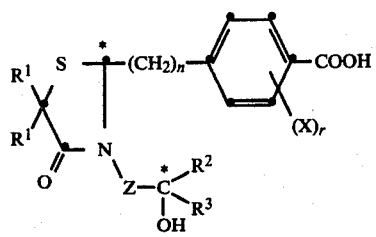

I

*denote chiral centers wherein
X is chloro or methyl,
r is 0, 1 or 2,
n is 3 or 4,
$R^1$ is hydrogen, deuterium or methyl,
Z is $-(CH_2)_2-$, $-(CH_2)_3-$, cis or trans propenylene or propynylene,
$R^2$ is H or $C_1-C_3$ alkyl
and
$R^3$ is 4-pentenyl, 5,5,5-trifluoropentyl or $C_3-C_7$ alkyl such that $R^2$ and $R^3$ are not the same
using camphanic acid or a camphor carboxylic acid as the resolving agent.

The process comprises
(a) preparing an ester of the formula:

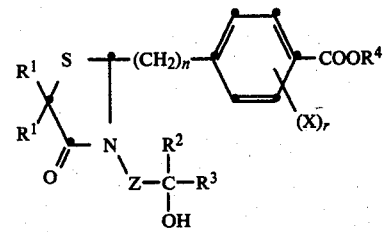

II wherein $R^4$ is $C_1-C_5$ alkyl or a phenyl substituted alkyl
(b) separating the II ester into its diastereomers
(c) treating a diastereomer from (b) with an optically active esterifying agent, E—COOH in the presence of a catalyst and a base to produce diastereomers of the formula:

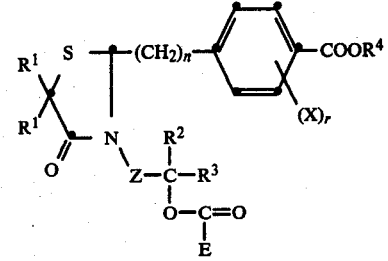

III wherein E—COOH is camphanic acid (or its anhydride) or camphor carboxylic acid (or its anhydride),
(d) separating the III diastereomers into individual diastereomers and
(e) hydrolyzing said diastereomer from (d) to obtain an individual enantiomer of I.

The formula I compounds have 2-chiral centers and accordingly comprise four stereoisomer configurations namely R,R; S,S; S,R and R,S. Thus, four enantiomers of formula I are available.

The following flow sheet illustrates the present resolution process:

FLOW SHEET

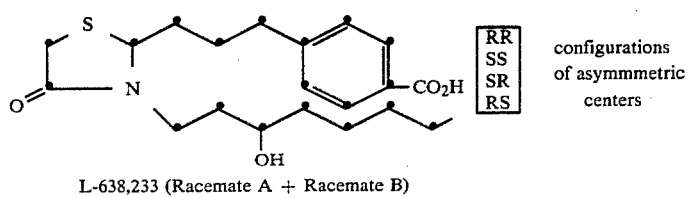

L-638,233 (Racemate A + Racemate B) — configurations of asymmetric centers: RR, SS, SR, RS

STEP A ↓

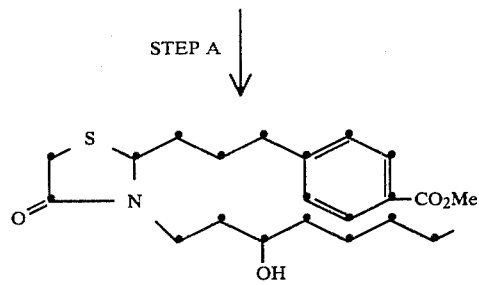

STEP B | HPLC

↙ ↘

Racemate A-Me ester [RR, SS]   Racemate B-Me ester [SR, RS]

STEP C-1 | Camphanic¹ Acid      STEP C-2 | Camphanic Acid

↓                                ↓

Rac. A - Me ester camphanate [RRR, SSR]     Rac. B - Me ester camphanate [SRR, RSR]

STEP D-1 | Fract. crystn.        Step D-2 | Fract. crystn.

↙ ↘                              ↓

(−)-diasteromer of Rac. A-Me ester Camphan. (1) [RRR]

(+)-diastereomer of Rac. A-Me est. camph (2) [SSR]

STEP E-1 | OH— H₂O       STEP E-2 | OH— H₂O

↓                         ↓

(−)-enantiomer of Racemate A (1) [RR]

(+)-enantiomer of Racemate A (2) [SS]

↓                         ↓

(−)-diastereomer of Rac. B-Me ester camph. (3)
SRR (+)-diastereomer of Rac. B-Me est. camp. (4)
RSR

FLOW SHEET

STEP E-3 │ OH—
        │ H₂O
        ▼
(−)-enantiomer of
Racemate B (3)
[SR]

-continued

STEP E-4 │ OH—
        │ H₂O
        ▼
(+)-enantiomer of
Racemate B (4)
[RS]

[1] Camphanic acid has the formula:

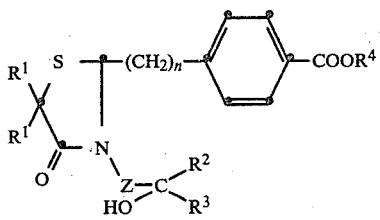

As outlined above in the flow sheet, the present process involves the following steps:

STEP A—PROTECTION OF THE BENZOIC ACID GROUP IN FORMULA I

The benzoic acid group is generally protected as an ester which can be removed easily via hydrolysis under mild conditions. Thus racemic formula I compound is treated with an esterifying agent such as, for example, an alcohol or an alkyl halide in the presence of a catalyst to form a benzoate of the structural formula:

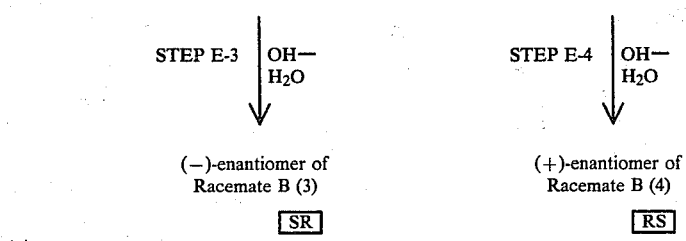

wherein $R^4$ is as defined in the following:

(1) Description which summarizes the scope of esterification with an alcohol; and
(2) Description which summarizes the scope of esterification with a halide.

(1) ESTERIFICATION OF THE BENZOIC ACID WITH AN ALCOHOL ALCOHOL ($R^4OH$)

(a) $C_{1-5}$ alkanol wherein $R^4$ is methyl, ethyl, isopropyl, tertiary butyl; isoamyl or the like; or
(b) phenyl-substituted methanol, e.g., benzyl alcohol, benzhydryl, or diphenylmethyl alcohol.

CATALYST UNDER ACIDIC CONDITIONS (a) sulfuric acid alone or in the presence of molecular sieves or arylsulfonic acids such as phenylsulfonic acid;
(b) hydrochloric acid or hydrobromic acid; or
(c) boron trifluoride-etherate.

CATALYST UNDER NEUTRAL OR BASIC CONDITIONS

N,N'-dicyclohexylcarbodiimide;
β-trichloromethyl-β-propiolactone;
N,N'-carbonyldiimidazole;
triphenylphosphine and diethylazodicarboxylate;
1-methyl-2-chloropyridinium iodide; or
6-chloro-1-p-chlorobenzenesulfonyloxybenzotriazole.

The preferred alcohol to be used is methanol or benzyl alcohol. The reaction is usually carried out in an excess amount of an alcohol in the presence of a catalyst. Under acidic conditions, the preferred catalysts are boron trifluoride etherate and sulfuric acid-molecular seive. A typical procedure involves the refluxing of the benzoic acid, in an alcohol with a suitable catalyst under anhydrous conditions. The refluxing continues with or without stirring until a substantial amount of the acid is converted to the ester. Usually it requires about 0.5 to 48 hours, preferably about 2 to 6 hours to obtain optimal yield. Generally, reaction temperatures vary with the boiling point of the alcohol being used but can be adjusted to a range from about 25° C. to about 120° C. with the optional addition of an inert solvent, for example, diethyl ether, methylene chloride, benzene, toluene or xylene. The preferred temperatures are about 35° C. to about 80° C., since the thiazolidine ring of the compounds of this invention normally survives at such mild temperatures.

(2) ESTERIFICATION WITH AN ALKYLHALIDE ($R^4hal$)

To esterify with $R^4hal$, the formula racemic acid is treated with a base to form a salt which is subsequently treated with $R^4hal$.

$R^4hal$ REACTANTS (a) $C_{1-5}$ alkylhalides wherein $R^4$ is methyl, ethyl, n-propyl, n-butyl or isoamyl; and X is chloro, bromo or iodo; or
(b) benzyl chloride or the like.

BASE FOR CONVERTING THE BENZOIC ACID TO A SALT (a) a mineral base such as sodium hydroxide, potassium hydroxide, calcium hydroxide, sodium carbonate or potassium carbonate; or
(b) an organic base such as ammonium hydroxide, quaternary ammonium hydroxide, for example, tetramethylammonium hydroxide, tetraethylammonium hydroxide or phenyltrimethylammonium hydroxide.

The reaction is preferably carried out in a polar, aprotic solvent such as dimethylformamide (DMF), N,N-dimethylacetamide (DMAC), dimethylsulfoxide (DMSO), or hexamethylphosphoramide (HMPA).

Other polar solvents may also be used. To minimize elimination, primary alkyl halides preferably methyl iodide or benzyl chloride are usually used and prolonged heating at high temperatures should be avoided. In most cases the reaction is conducted at about 0°-100° C. preferably at about 10°-40° C. For example, the reaction is stirred and maintained at about 25° C. until it is substantially complete, usually in about 1 to 48 hours, preferably about 2 to about 10 hours under optimal conditions.

STEP B—SEPARATION OF STEP A ESTERS

Separation of the esters prepared in Step A may be effected by any conventional means. High pressure liquid chromatography (HPLC) affords a suitable means for separation.

STEP C—FORMATION OF DIASTEREOMERS FOR RESOLUTION

This step involves esterification of the product from Step B with an optically active acid resolving agent generally in the presence of a base and a catalyst. Useful resolving agents, catalysts and bases are described below:

1. Resolving agents
   (+) or (−)-camphanic acid
   (+) or (−)-camphanyl anhydride
   (+) or (−)-camphorcarboxylic acid
2. Catalyst
   N,N'-dicyclohexylcarbodiimide (DCC)
   β-tri-chloromethyl-β-propiolactone
   N,N'-carbonyldiimidazole
   1-methyl-2-halopyridinium iodide (halo=F, Cl, Br or I)
3. Base
   a trialkylamine ($R_3N$) wherein R is alkyl especially $C_{1-5}$ alkyl such as methyl, ethyl or butyl
   pyridine
   4-dimethylaminopyridine
   2,4,6-collidine
   2,6-lutidine
   quinoline

STEP D—SEPARATION OF THE DIASTEREOISOMERS

Fractional recrystallization is used to separate the diastereoisomers from Step C having the formula:

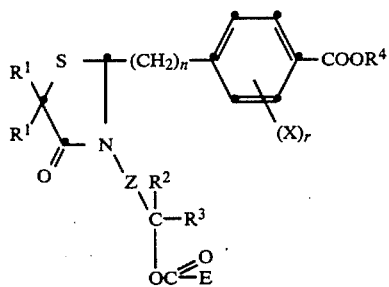

III

Typically, a suitable organic solvent is selected for successive recrystallization until a pure diastereoisomer is isolated. The solvents usually include water, acetonitrile, $C_{1-3}$ alkanol such as methanol or ethanol, acetone, methylacetate, ethylacetate, methylene chloride, ethyl ether, chloroform, doxane, carbon tetrachloride, toluene, benzene, petroleum ether, n-pentane, n-hexane, cyclohexane or a mixture thereof. The preferred solvent for the camphanyl or camphorcarbonyl esters of Step (C) is methylene chloride, chloroform, ethylacetate or a mixture thereof.

STEP E—HYDROLYSIS

Hydrolysis of the highly hindered Formula III esters is difficult. A few representative hydrolysis procedures which are useful are described below:

| | Hydrolysis Systems | |
|---|---|---|
| | Catalyst | Solvent |
| (1) | sodium hydroxide (aqueous solution) | tetrahydrofuran-methanol-water |
| (2) | potassium hydroxide (aqueous solution) | tetrahydrofuran-methanol-water |
| (3) | potassium hydroxide (pellets) and dicyclohexyl-18-crown-6 (naked hydroxide ion) or sodium hydroxide pellets with other crown ethers | toluene or benzene |
| (4) | lithium tetrahydroboron | tetrahydrofuran, or hexamethyl phosphoramide (HMPA) or mixture thereof |

The hydrolysis is usually conducted at about 25° C. to about 120° C. depending on the solvent being used. For example, hydrolysis involving the naked hydroxyl ion (KOH-crown ether) is carried out preferably at about 40° C. to about 60° C. The reaction is continued with vigorous agitation until it is substantially complete, usually about 2 to 48 hours, preferably about 5 to about 24 hours.

The following example illustrates the process of the present invention. Temperatures are in degrees Celsius.

EXAMPLE 1

(A) Preparation of Methyl 4-{3-[3-(3-Hydroxyoctyl)-4-oxo-2-thiazolidinyl]-propyl}benzoate A solution of racemic 4-{3-[3-(3-hydroxyoctyl)-4-oxo-2-thiazolidinyl]propyl}-benzoic acid (13.13 g; 0.03336 mole) in dimethylformamide (66 ml) is treated with potassium carbonate (9.22 g; 0.06672 mole) and methyliodide (5.68 g; 0.04003 mole) and the resulting mixture is stirred at room temperature for 22 hours.

The reaction mixture is poured into cold water (330 ml). The oily layer is extracted with ether. The combined extracts are washed well with water and dried over magnesium sulfate. The solvent is removed under vacuum to give the methyl 4-{3-[3-(3-hydroxyoctyl)-4-oxo-2-thiazolidinyl]propyl}benzoate racemate as an orange oil, yield 13.60 g.

(B) Separation of the Two Racemic Modifications of Methyl 4-{3-[3-(3-hydroxyoctyl)-4-oxo-2-thiazolidinyl]-propyl}benzoate The two racemic modifications that comprise methyl 4-{3-[3-(3-hydroxyoctyl-4-oxo-2-thiazolidinyl]propyl}-benzoate as obtained above in A are separated by liquid chromatography using a Prep LC/System 500 liquid chromatograph manufactured by Waters Associate, Inc. The chromatographic column in this instrument is a Prep PAK-500/$C_{18}$ silica cartridge with dimensions 5.7×30 cm. The solvent mixture used is hexane-isopropyl alcohol, 95:5 (v/v). Thirteen g of the mixed racemates of the methyl ester after elution with 60 L of the solvent system gives 4.8 g of a front running fraction designated Racemate B-methyl ester and 6.9 g of a slower running fraction designated Racemate A-methyl ester. The two fractions can also be differentiated by thin layer chromatography on silica with 2% methanol in chloroform (v/v) as the mobile phase. In this system, Racemate B-methyl ester has $R_f$ 0.32, and Racemate A-methyl ester has $R_f$ 0.28.

(C-1) Preparation of Diastereomeric Camphanates from Racemate A of Methyl 4-{3-[3-(3-hydroxyoctyl)-4-oxo-2-thiazolidinyl]-propyl}benzoate N,N'-Dicyclohexylcarbodiimide (6.2 g, 30 mmole) in $CH_2Cl_2$ is added to a solution at 0° C. of Racemate A of methyl 4{3-[3-(3-hydroxyoctyl)-4-oxo-2-thiazolidinyl]-propyl}benzoate (10.0 g, 24.6 mmole), (1S)-(—)-ω-camphanic acid (5.39 g, 27.2 mmole) and 4-dimethylaminopyridine (1.5 g, 12.3 mmole) in $CH_2Cl_2$ (25 ml). The mixture is stirred at 27° C. for 6 hours. Precipitated dicyclohexylurea is removed by filtration. The filtrate is washed with 0.1 N hydrochloric acid and dried. Removal of solvent gave the crude mixed diastereomeric camphanates of Racemate A-methyl ester.

(C-2) Preparation of Diastereomeric Camphanates from Racemate B of Methyl 4-{3-[3-(3-hydroxyoctyl)-4-oxo-2-thiazolidinyl]-propyl}benzoate By following the procedure described in Step C-1 but substituting Racemate B-methyl ester for the Racemate A-methyl ester there is obtained the crude mixed diastereomeric camphanates of Racemate B-methyl ester.

(D-1) Isolation of the Levorotatory Diastereomeric Camphanate of Racemate A of Methyl 4-{3-[3-(3-hydroxyoctyl)-4-oxo-2-thiazolidinyl[-propyl}benzoate The crude mixed diastereomeric camphanates of Racemate A-methyl ester (Step C-1) are triturated with 1:1 ethyl acetate-hexane (100 ml of solvent mixture per 15 g of esters). The insoluble material is collected on a filter. The filtrate containing the bulk of the dextrorotatory diastereomer is set aside. The solid is recrystallized three times from ethyl acetate to give the levorotatory diastereomeric camphanate of Racemate A-methyl ester (chemical name: (—)-diastereomer of racemate A methyl 4-{3-[3-(3-((1S)-ω-camphanyloxy)octyl)-4-oxo-2-thiazolidinyl]propyl}benzoate).

(D-2) Isolation of the Dextrorotatory Diastereomeric Camphanate of Racemate A of Methyl 4-{3-[3-(3-hydroxyoctyl)-4-oxo-2-thiazolidinyl]-propyl}benzoate Evaporation of solvents from the filtrate obtained by trituration of mixed diastereomeric camphanate of racemate A-methyl ester gives an oil which crystallizes on standing. This solid is recrystallized three times from ethyl acetate to yield the dextrorotatory diastereomeric camphanate of racemate A-methyl ester. (Chemical name: (+)-diastereomer of racemate A methyl 4-{3-[3-(3-((1S)-ω-camphanyloxy-octyl)-4-oxo-2-thiazolidinyl]-propyl}benzoate).

(D-3) Isolation of the Levorotatory Diastereomeric Camphanate of Racemate B of Methyl 4-{3-[3-(3-hydroxyoctyl)-4-oxo-2-thiazolidinyl]-propyl}benzoate Treatment of the crude mixed diastereomeric camphanates of Racemate B-methyl ester (Step C-2) exactly as in D-1 yields the levorotatory diastereomeric camphanate of Racemate B-methyl ester (chemical name: (—)-diastereomer or racemate B-methyl 4-3-[3-(3-((1S)-ω-camphanyloxy)octyl-4-oxo-2-thiazolidinyl]propyl benzoate).

(D-4) Isolation of the Dextrorotatory Diastereomeric Camphanate of Racemate B of Methyl 4-{3-[3-(3-hydroxyoctyl)-4-oxo-2-thiazolidinyl]-propyl}benzoate Treatment of the filtrate from the isolation of the camphanate of D-3 exactly as described in Step D-2 yields the dextrorotatory diastereomeric camphanate of Racemate B-methyl ester (chemical name: (+)-diastereomer or racemate B-methyl 4-{3-[3-(3-((1S)-ω-camphanyloxy)octyl)-4-oxo-2-thiazolidinyl]-propyl}benzoate.

(E-1) Preparation of the (—)-Enantiomer of Racemate A of 4-{3-[3-(3-hydroxyoctyl)-4-oxo-2-thiazolidinyl]-propyl}benzoic acid Potassium hydroxide (finely crushed pellets) (3.83 g, 68.3 mmoles) is added to toluene (100 ml). The mixture is stirred and treated with the levorotatory diastereomeric camphanate of Racemate A-methyl ester (D-1) (4 g, 6.82 mmoles) and dicyclohexyl-18-crown-6 (12.7 g, 34.2 mmole). The mixture is then stirred and heated at 40° C. for 1 hour. Water (80 ml) is added to the reaction mixture and stirring at 40° C. is continued for 45 hours. The mixture is then poured into 1 N hydrochloric acid (200 ml). The toluene layer is separated, washed with water and dried. The solvent is evaporated at reduced pressure. The residual oil is triturated with acetonitrile to give the waxy solid (—)-enantiomer of racemate A of 4-{3-[3-(3-hydroxyoctyl)-4-oxo-2-thiazolidinyl]-propyl}benzoic acid.

(E-2) Preparation of the (+)-Enantiomer of Racemate A of 4-{3-[3-(3-hydroxyoctyl)-4-oxo-2-thiazolidinyl]-propyl}benzoic acid Hydrolysis of the dextrorotatory diastereomeric camphanate of Racemate A-methyl ester (Step D-2) exactly as described in Step E-1 yields the waxy solid (+)-enantiomer of Racemate A of 4-{3-[3-(3-hydroxyoctyl)-4-oxo-2-thiazolidinyl]propyl}benzoic acid.

(E-3) Preparation of the (—)-Enantiomer of Racemate B of 4-{3-[3-(3-hydroxyoctyl)-4-oxo-2-thiazolidinyl]-propyl}benzoic acid Hydrolysis of the levorotatory diastereomeric camphanate of Racemate B-methyl ester (Step D-3) exactly as described in Step E-1 yields the waxy solid (—)-enantiomer of Racemate B of 4-{3-[3-(3-hydroxyoctyl)-4-oxo-2-thiazolidinyl]propyl}benzoic acid.

(E-4) Preparation of the (+)-Enantiomer of Racemate B of 4-{3-[3-(3-hydroxyoctyl)-4-oxo-2-thiazolidinyl]-propyl}benzoic acid Hydrolysis of the dextrorotatory diastereomeric camphanate of Racemate B-methyl ester (Step D-4) exactly as described in Step E-1 yields the waxy solid (+)-enantiomer of Racemate B of 4-{3-[3-(3-hydroxyoctyl)-4-oxo-2-thiazolidinyl]propyl}benzoic acid.

Following substantially the same procedure as described in Example 1 but substituting for the racemic benzoic acid in the following compounds:

4-{3-[3-(3-hydroxynonyl)-4-oxo-2-thiazolidinyl]-propyl}benzoic acid;

4-{3-[3-(3-hydroxydecyl)-4-oxo-2-thiazolidinyl]-propyl}benzoic acid;

4-{3-[3-(3-hydroxy-4,4-dimethyloctyl)-4-oxo-2-thiazolidinyl]propyl}benzoic acid;

4-{3-[3-(3-hydroxy-7-octenyl)-4-oxo-2-thiazolidinyl]-propyl}benzoic acid;

4-{3-[3-(3-hydroxy-8,8,8-trifluorooctyl)-4-oxo-2-thiazolidinyl]propyl}benzoic acid or 4-{3-[3-(3-hydroxy-3-methyloctyl)-4-oxo-2-thiazolidinyl]propyl}benzoic acid, there are obtained the corresponding enantiomers:

R,R; R,S; S,R or S,S-4-{3-[3-(3-hydroxynonyl)-4-oxo-2-thiazolidinyl]propyl}benzoic acid;

R,R; R,S; S,R or S,S-4-{3-[3-(3-hydroxydecyl)-4-oxo-2-thiazolidinyl]propyl}benzoic acid;

R,R; R,S; S,R or (−)-4-{3-[3-(3-hydroxy-4,4-dimethyloctyl)-4-oxo-2-thiazolidinyl]propyl}benzoic acid;

R,R; R,S; S,R or S,S-4-{3-[3-(3-hydroxy-7-octenyl)-4-oxo-2-thiazolidinyl]propyl}benzoic acid;

R,R; R,S; S,R or S,S-4-{3-[3-(3-hydroxy-8,8,8-trifluorooctyl)-4-oxo-2-thiazolidinyl]propyl}benzoic acid or R,R; R,S; S,R or S,S-4-{3-[3-(3-hydroxy-3-methyloctyl)-4-oxo-2-thiazolidinyl]propyl}benzoic acid.

In addition to the resolution process, other embodiments of the present invention are (1) the diastereomer esters of Formula III and (2) the individual enantiomers of the formula I compound which have pharmaceutical activity e.g. as renal vasodilators.

What is claimed is:

1. The diastereomer having the formula wherein
(1) X is chlorine or methyl;
(2) n is 0, 1 or 2;
(3) n is 3 or 4;
(4) $R^1$ is hydrogen, deuterium or methyl;
(5) E is (6) $R^2$ is H or $C_1$–$C_3$ alkyl;
(7) $R^3$ is 4-pentenyl, 5,5,5-trifluoropentyl or $C_3$–$C_7$ alkyl and
(8) Z is $(CH_2)_2$, $(CH_2)_3$, cis or transpropenylene or propynylene.

2. The diastereomer of claim 1 having the formula:

3. The diastereomer of claim 2 wherein $$-\overset{O}{\underset{\|}{C}}-E$$

is camphanoyl and $R^4$ is $CH_3$.

* * * * *